United States Patent
Winter et al.

(10) Patent No.: US 9,227,929 B2
(45) Date of Patent: Jan. 5, 2016

(54) SULFONATION IN CONTINUOUS-FLOW MICROREACTORS

(75) Inventors: Marc Winter, Saint Nom la Breteche (FR); Feixia Zhang, Shanghai (CN)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 13/989,277

(22) PCT Filed: Nov. 22, 2011

(86) PCT No.: PCT/US2011/061744
§ 371 (c)(1),
(2), (4) Date: May 23, 2013

(87) PCT Pub. No.: WO2012/074822
PCT Pub. Date: Jun. 7, 2012

(65) Prior Publication Data
US 2013/0245315 A1    Sep. 19, 2013

(30) Foreign Application Priority Data
Nov. 29, 2010   (EP) ..................................... 10306314

(51) Int. Cl.
*C07C 303/20* (2006.01)
*C07C 303/06* (2006.01)

(52) U.S. Cl.
CPC ............. *C07C 303/20* (2013.01); *C07C 303/06* (2013.01)

(58) Field of Classification Search
None
See application file for complete search history.

(56) References Cited

U.S. PATENT DOCUMENTS

| 6,515,189 B1 * | 2/2003 | Harston et al. ................ 568/939 |
| 6,747,178 B1 | 6/2004 | Harston et al. ................ 570/175 |
| 6,935,768 B2 * | 8/2005 | Lowe et al. ................ 366/167.1 |
| 2004/0059126 A1 * | 3/2004 | Rauchschwalbe et al. 548/310.7 |
| 2005/0276160 A1 * | 12/2005 | Woehl et al. ................... 366/336 |

(Continued)

FOREIGN PATENT DOCUMENTS

CN          101607925        3/2013

OTHER PUBLICATIONS

Database Caplus Chemical Abstracts Service, Columbus, Ohio, US; Database Accession No. 2007:355250, Abstract of CN 1935786, Tang et al., Mar. 28, 2007.*
Machine Translation of CN1935786.*
Ind. Eng. Chem. Res. 2005, 44, 9750-9769.*
International Searching Authority; International Search Report; Mailing Date: Apr. 2, 2012; pp. 1-3.

(Continued)

*Primary Examiner* — Karl J Puttlitz
(74) *Attorney, Agent, or Firm* — Gregory V. Bean (57) ABSTRACT

A continuous flow process for sulfonating 1,2.diaminobenzene comprises introducing a sulfonation mixture into a microreactor inlet of a continuous flow microreactor to produce a flow of the sulfonation mixture through the continuous flow microreactor. The sulfonation mixture comprises 1,2 aminobenzene dissolved in a molar excess of sulfuric acid. The continuous flow microreactor comprises one or more individual fluidic modules each having various features with respect to channel width and thermal management. The process further comprises maintaining a reaction temperature of from about 150.230 deg C. in at least a portion of the individual fluidic modules while the sulfonation mixture flows from the microreactor inlet to the microreactor outlet. Thereupon, the sulfonation mixture is received from the microreactor outlet. Finally, a sulfonated reaction product is precipitated out of the sulfonation mixture received from the microreactor outlet. The sulfonated reaction product is 3,4.diaminosulfonic acid, free of doubly sulfonated impurities.

18 Claims, 4 Drawing Sheets

(56) References Cited

U.S. PATENT DOCUMENTS

| | | | |
|---|---|---|---|
| 2007/0256736 A1* | 11/2007 | Tonkovich et al. | 137/92 |
| 2009/0028763 A1* | 1/2009 | Lavric et al. | 422/189 |
| 2009/0074627 A1* | 3/2009 | Fitzgerald et al. | 422/129 |
| 2009/0326279 A1 | 12/2009 | Tonkovich et al. | 568/487 |

OTHER PUBLICATIONS

Machine Translation CN101607925.

Jinxia et al; "Application of Microfluidic Reactors on Synthesis Reactions"; Progress in Chemistry; vol. 20 No. 1, Jan. 31, 2008.

CN201180057254.1 Search Report.

* cited by examiner

FIG. 5

SULFONATION IN CONTINUOUS-FLOW MICROREACTORS

This application claims the benefit of priority under 35 USC §119 to European Patent Application Serial No. 10306314.5 filed Nov. 29, 2010 the content of which is relied upon and incorporated herein by reference in its entirety.

TECHNICAL FIELD

The present invention relates to a sulfonation process and, more particularly, to a sulfonation process for converting 1,2-diaminobenzene to 3,4-diaminobenzenesulfonic acid in a continuous-flow microreactor.

BACKGROUND 3,4-diaminobenzenesulfonic acid (DBSA), also known as orthaminic acid, is a useful compound having applications in the fields of crop protection, pharmaceutical preparation, cosmetics, and dyes. Particularly for pharmaceutical preparations and in cosmetics, a strong need exists for having highly pure DBSA. Common routes for synthesizing DBSA involve the sulfonation of 1,2-diaminobenzene (DAB). However, known large-scale sulfonation processes for DAB suffer from the disadvantages of inadequate yield, impure sulfonation products such as doubly sulfonated analogs of DBSA, costly apparatus requiring extreme pressure-resistance and corrosion-resistance in the presence of acids such as hydrochloric acid and sulfuric acid, and needs for energy-inefficient distillation steps.

SUMMARY

The present inventors have found that various configurations of a microfluidic reactor can eliminate the disadvantages of the processes described above. The process involving a continuous-flow reactor having sequentially connected fluidic modules, as described in the present disclosure, has been found to produce quantitative yields of pure DBSA without impurities.

Thus, according to embodiments of the present invention, a continuous-flow process is described for sulfonating 1,2-diaminobenzene. The continuous-flow process comprises introducing a sulfonation mixture into a microreactor inlet of a continuous-flow microreactor to produce a flow of the sulfonation mixture through the continuous-flow microreactor. The sulfonation mixture comprises 1,2-aminobenzene dissolved in a molar excess of sulfuric acid. The continuous-flow microreactor comprises one individual fluidic module or a plurality of sequentially connected individual fluidic modules each having various features with respect to channel width and thermal management. The process further comprises maintaining a reaction temperature of from about 160° C. to about 280° C. in at least a portion of the individual fluidic modules while the sulfonation mixture flows from the microreactor inlet to the microreactor outlet. Thereupon, the sulfonation mixture is received from the microreactor outlet. Finally, a sulfonated reaction product is precipitated out of the sulfonation mixture received from the microreactor outlet.

These and other features, aspects, and advantages of the present invention will become better understood with reference to the following description, appended claims, and accompanying drawings.

BRIEF DESCRIPTION OF THE DRAWINGS

Though the specification concludes with claims particularly pointing out and distinctly claiming the invention, it is believed that the present invention will be better understood from the following description taken in conjunction with the accompanying drawings, in which:

DETAILED DESCRIPTION

Features and advantages of the invention will now be described with occasional reference to specific embodiments. However, the invention may be embodied in different forms and should not be construed as limited to the embodiments set forth herein. Rather, these embodiments are provided so that this disclosure will be thorough and complete and will fully convey the scope of the invention to those skilled in the art.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. One of ordinary skill in the art will understand that any numerical values inherently contain certain errors attributable to the measurement techniques used to ascertain the values.

As used herein, the terms "horizontal" and "vertical" are relative terms only, are indicative of a general relative orientation only, and do not necessarily indicate perpendicularity. These terms also may be used for convenience to refer to orientations used in the figures, which orientations are used as a matter of convention only and are not intended as characteristic of the devices shown. The present invention and the embodiments thereof to be described herein may be used in any desired orientation. Moreover, horizontal and vertical walls need generally only be intersecting walls, and need not be perpendicular.

Without limitation, in the microfluidic devices described herein, the reactant passage and its portion constituted by a flow path configuration are extended generally in a horizontal plane defined by vertical walls. In this context, the "width" refers to a direction perpendicular to the flow direction and parallel to said horizontal plane of the flow path configuration. The "height" refers to a direction perpendicular to the flow direction and perpendicular to said horizontal plane of the flow path configuration. The "length" refers to a direction parallel to the flow direction and parallel to said horizontal plane of the flow path configuration.

As used herein, the term "microreactor" refers to a device for performing chemical or physical processes within a series of modular or permanently assembled fluidic modules. The fluidic modules themselves may be characterized as microfluidic devices. Microfluidic devices, as understood herein, include fluidic devices over a scale ranging from microns to a few millimeters—that is, devices with fluid channels having a smallest dimension in the range of microns to a few millimeters, preferably in the range of from tens of microns to about 2 millimeters. Partly because of their characteristically low total process fluid volumes and characteristically high surface to volume ratios, microfluidic devices are useful in microreactors to perform difficult, dangerous, or even otherwise impossible chemical reactions and processes in a safe, efficient, and environmentally-friendly way.

According to various embodiments, a continuous-flow process for sulfonating 1,2-diaminobenzene comprises introducing a sulfonation mixture into a microreactor inlet of a continuous-flow microreactor to produce a flow of the sulfonation mixture through the continuous-flow microreactor. The continuous-flow microreactor comprises one individual fluidic module or a plurality of sequentially connected individual fluidic modules. As used herein, the term "sequentially connected individual fluidic modules" means that an inlet of each module is connected to either a reactant source or an outlet of another module and that an outlet of each module either represents the end of the sequence of modules or is connected to an inlet of another module. In preferred embodiments, the individual fluidic modules are sequentially connected in series. Nevertheless, it is contemplated that the individual modules may be configured in a parallel manner, such that an outlet of a first module may be connected to inlets of more than one other module.

In the continuous-flow microreactor, each individual fluidic module comprises a continuous channel defined in a reaction volume of the individual fluidic module. The continuous channel defines a tortuous fluidic flowpath from a module inlet of the individual fluidic module to a module outlet of the individual fluidic module. As used herein, the term "tortuous fluidic flowpath" refers to a flowpath defined between substantially parallel walls in the horizontal direction and between substantially parallel surfaces in the vertical direction, such that the flowpath comprises a plurality of bends having bend angles of at least 90°, preferably of about 180°. The plurality of bends in this regard results in a change of fluid-flow direction and, in preferred embodiments, complete reversal of the fluid-flow direction with respect to an edge of the individual fluidic module.

In example embodiments, the continuous channel has a continuous-channel width of from about 0.4 mm to about 6 mm, preferably from about 0.7 mm to about 1.1 mm. In example embodiments, the continuous channel may have a cross-sectional area of about 0.4 $mm^2$ to about 60 $mm^2$, preferably from about 0.4 $mm^2$ to about 30 $mm^2$, more preferably from about 0.7 $mm^2$ to about 15 $mm^2$, still more preferably from about 0.7 $mm^2$ to about 6 $mm^2$.

The continuous-flow microreactor comprises one individual fluidic module or a plurality of sequentially connected individual fluidic modules. One individual fluidic module is an inlet module, such that the module inlet of the inlet module defines the microreactor inlet. One individual fluidic module further is an outlet module, such that the module outlet of the outlet module defines a microreactor outlet. At least one individual fluidic module is a residence module providing fluidic communication between the inlet module and the outlet module. The microreactor outlet is in fluidic communication with the microreactor inlet through the continuous channels of each of the individual fluidic modules. As such, if the continuous-flow microreactor comprises only one individual fluidic module, the one individual fluidic module itself functions as the inlet module, the outlet module, and the one or more residence modules. Likewise, if the continuous-flow microreactor comprises a plurality of sequentially connected individual fluidic modules, any single individual fluidic module from among the plurality of sequentially connected individual fluidic modules may function simultaneously as the inlet module and a residence module, or as the outlet module and a residence module, for example.

Figure 1:
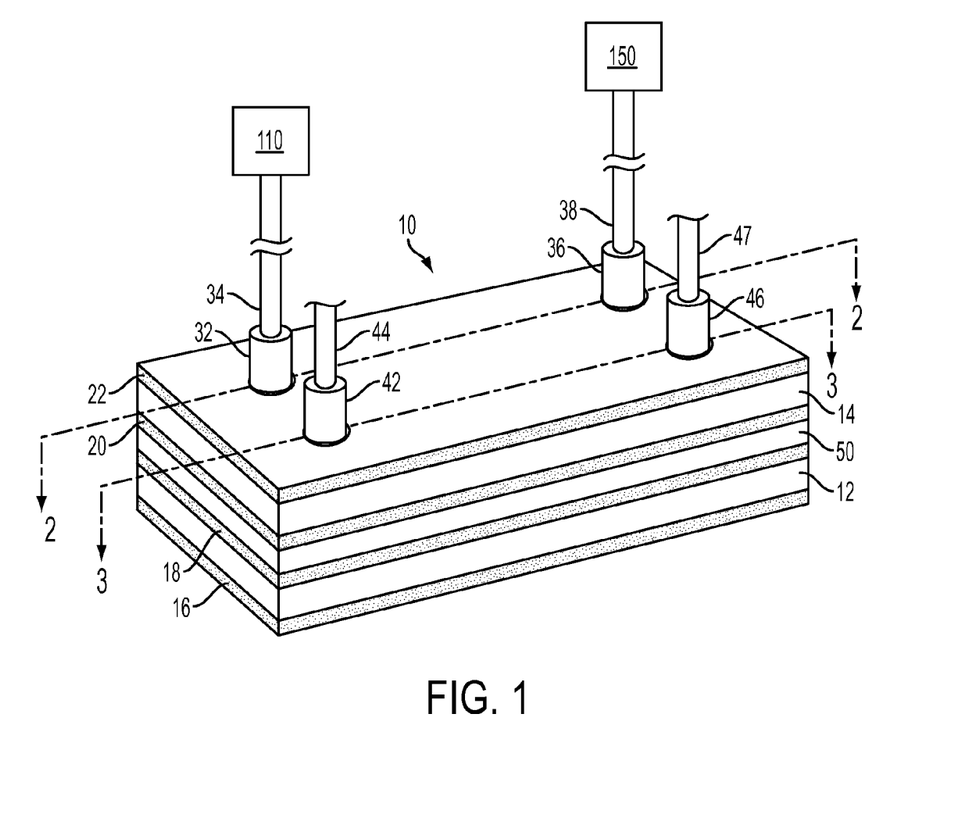
FIG. 1 is a schematic perspective representation of an individual fluidic module of a continuous-flow microreactor according to embodiments of the present invention.

Non-limiting example embodiments of the individual fluidic modules are shown in FIGS. 1-4. Referring with particularity to FIG. 1, an individual fluidic module 10 is shown in schematic perspective, not to scale. In general terms, the individual fluidic module 10 may comprise at least two thermal-control volumes, depicted in FIG. 1 as a first thermal-control volume 12 and a second thermal-control volume 14. The first thermal-control volume 12 and the second thermal-control volume 14 comprise one or more thermal-control passages (not shown in FIG. 1, but described below with respect to FIG. 2) positioned or structured within the respective thermal-control volume. The first thermal-control volume 12 is limited in the vertical direction by horizontal walls, specifically by a module bottom wall 16 and a reaction-volume bottom wall 18. The second thermal-control volume 14 is limited in the vertical direction by horizontal walls, specifically by a reaction-volume top wall 20 and a module top wall 22. The individual fluidic module 10 comprises a reaction volume 50 interposed between the reaction-volume top wall 20 and the reaction-volume bottom wall 18.

The individual fluidic module 10 may be made from any material resistant to corrosion by the sulfonation mixture containing sulfuric acid. In example embodiments, the individual fluidic module 10 may be made from polymeric materials such as polytetrafluoroethylene (PTFE), for example, or from corrosion-resistant metals such as titanium, for example. The individual fluidic module 10 is desirably made from one or more material selected from glass, glass-ceramic, and ceramic. Processes for preparing fluidic modules from glass sheets, forming horizontal walls, with molded and consolidated frit positioned between the sheets forming vertical walls, are disclosed, for example, in U.S. Pat. No. 7,007,709, "Microfluidic Device and Manufacture Thereof" Fabrication is not limited to the method described therein. The individual fluidic modules described in the present disclosure may also include layers additional to those shown, if desired.

Each individual fluidic module 10 comprises at least four fluidic connections. The fluidic connections include a module reactant inlet 32, a module reactant outlet 36, a thermal-control fluid inlet 42, and a thermal-control fluid outlet 46. It will be understood that the actual positions of the fluidic connections are depicted in FIG. 1 for non-limiting illustrative purposes only. Any of the fluidic connections may be disposed anywhere on the outer surfaces of the individual fluidic module 10, including on either the module top wall 22, the module bottom wall 16, or both. In embodiments described below, the individual fluidic module 10 may further comprise additional fluidic connections, such as a quenching-fluid inlet (not shown). The additional fluidic connections, when present, are in fluidic communication with the reaction volume 50.

The module reactant inlet 32 is in fluidic communication with the reaction volume 50 and also with a reactant source 110 through a delivery conduit 34. During the continuous-flow process, the reactant source 110 is the source of sulfonation mixture to be introduced into the continuous-flow microreactor. The module reactant outlet 36 is in fluidic communication with the reaction volume 50 and also with a receiving vessel 150 through an exit conduit 38. The fluidic communication of the module reactant inlet 32 with the reactant source 110 is not necessarily established through a direct connection. Rather, the delivery conduit 34 may deliver the sulfonation mixture from the exit conduit of a different individual fluidic module (not shown) disposed between the individual fluidic module 10 and the reactant source 110. Likewise, the fluidic communication of the module reactant outlet 36 with the receiving vessel 150 is not necessarily established through a direct connection. Rather, the exit conduit 38 may convey the sulfonation mixture to a different individual fluidic module (not shown) disposed between the individual fluidic module 10 and the receiving vessel 150.

The thermal-control fluid inlet 42 and the thermal-control fluid outlet 46 both are in fluidic communication with the first thermal-control volume 12 and the second thermal-control volume 14. The thermal-control fluid inlet 42 is connected to a thermal-control fluid delivery conduit 44. The thermal-control fluid outlet 46 is connected to a thermal-control fluid exit conduit 47. The thermal-control fluid delivery conduit 44 and the thermal-control fluid exit conduit 47 convey a thermal-control fluid into and out of the individual fluidic module 10.

Figure 2:
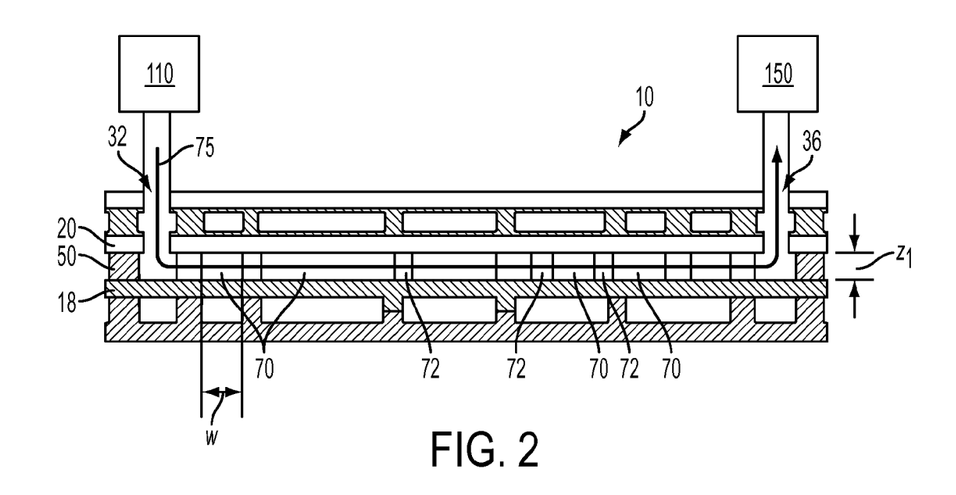
FIG. 2 is a cross-sectional view of the individual fluidic module of FIG. 1, highlighting a flow path for a sulfonation mixture, including schematic representation of fluidic communication with a reactant source and a receiving vessel.
Figure 3:
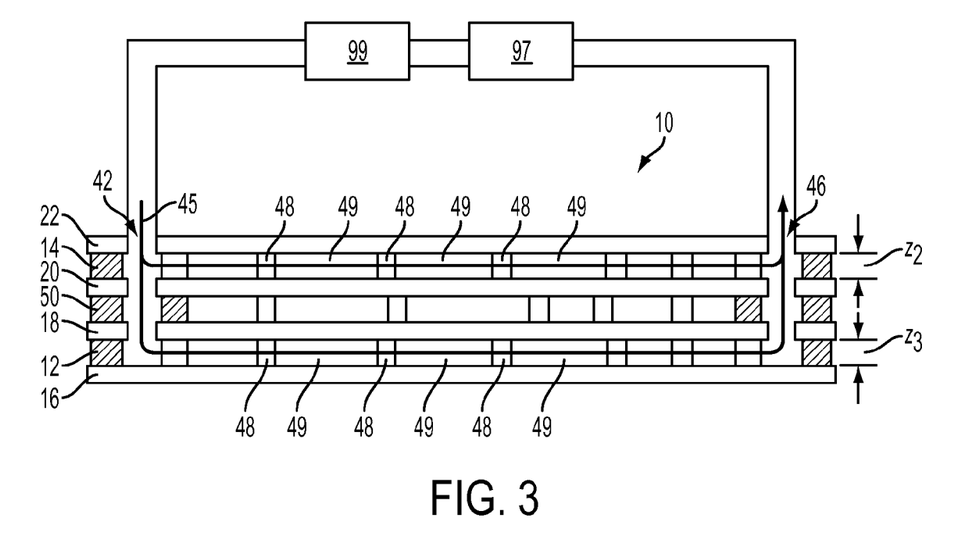
FIG. 3 is a cross-sectional view of the individual fluidic module of FIG. 1, highlighting a flow path for a thermal-control fluid, including schematic representation of additional thermal-management devices.

The internal structure of the individual fluidic module 10 is more clearly understood with reference to FIGS. 2 and 3. In FIG. 2, for example, the structure of the reaction volume 50 is illustrated. The reaction volume 50 is defined between the reaction-volume bottom wall 18 and the reaction-volume top wall 20. The reaction-volume top wall is supported over the reaction-volume bottom wall 18 by reaction-volume supports 72 (for clarity, not all are labeled). In the particular cross-section shown in FIG. 2, portions of the continuous channel 70 are visible as defined in a horizontal direction between two of the reaction-volume supports 72 and in a vertical direction between the reaction-volume bottom wall 18 and the reaction-volume top wall 20. The continuous channel 70 has a substantially constant height in a direction perpendicular to the reaction-volume supports 72. The continuous channel 70 has a continuous-channel width w and a continuous-channel depth $z_1$.

Also shown schematically in FIG. 2 is a reactant fluid path 75, along which fluidic communication among the reactant source 110, the module reactant inlet 32, the reaction volume 50, the continuous channel 70, the module reactant outlet 36, and the receiving vessel 150 is accomplished. As described above, the fluidic communication between the reactant source 110 and the module reactant inlet 32 need not be a direct connection, just as the fluidic communication between the module reactant outlet 36 and the receiving vessel 150 also need not be through a direct connection.

The structures of the first thermal-control volume 12 and the second thermal-control volume 14 are illustrated in FIG. 3. The first thermal-control volume 12 is defined between the module bottom wall 16 and the reaction-volume bottom wall 18 and has a first control-volume height $z_3$. The second thermal-control volume 14 is defined between the module top wall 22 and the reaction-volume top wall 20 and has a second control-volume height $z_2$. In preferred embodiments $z_2$ is approximately equal to $z_3$. The reaction volume 50 is interposed between the first thermal-control volume 12 and the second thermal-control volume 14, such that the reactor volume is in thermal communication with the first thermal-control volume 12 and the second thermal-control volume 14 through the reaction-volume bottom wall 18 and the reaction-volume top wall 20, respectively. The two thermal-control volumes 12, 14 are supported by control-volume supports 48. Thermal-control fluid conduits 49 are defined in a horizontal direction by the control-volume supports 48 that are adjacent to one another.

Shown schematically in FIG. 3 is a thermal-control fluid path 45, along which fluidic communication among the thermal-control fluid inlet 42, the first thermal-control volume 12, the second thermal-control volume 14, the thermal-control fluid conduits 49, and the thermal-control fluid outlet 46 is accomplished. These components also are in fluidic communication with a control-fluid thermostat 97 and a control-fluid pump 99. The control-fluid thermostat 97 may comprise, for example, a temperature monitoring device (not shown) such as a thermometer and/or a thermal management device (not shown) such as a heat exchanger, a heater, or a cooling device. The control-fluid thermostat 97 may be electrically connected to the control-fluid pump 99, such that the control-fluid temperature monitor and the control-fluid pump 99 may cooperate to circulate thermal-control fluid along the thermal-control fluid path 45 at a desired temperature, rate, and pressure.

In a plane extending perpendicularly into the plane of FIG. 3, the two thermal-control volumes 12, 14 may comprise a variety of diversion features (not shown) for ensuring an ideal exchange of heat between the two thermal-control volumes 12, 14 and the reaction volume 50. In preferred embodiments, the two thermal-control volumes 12, 14 may be configured according to one or more structures disclosed in European Pat. Appl. EP 2 193 844, entitled "Heat exchanger for microstructures," assigned to Corning, Incorporated.

Figure 4:
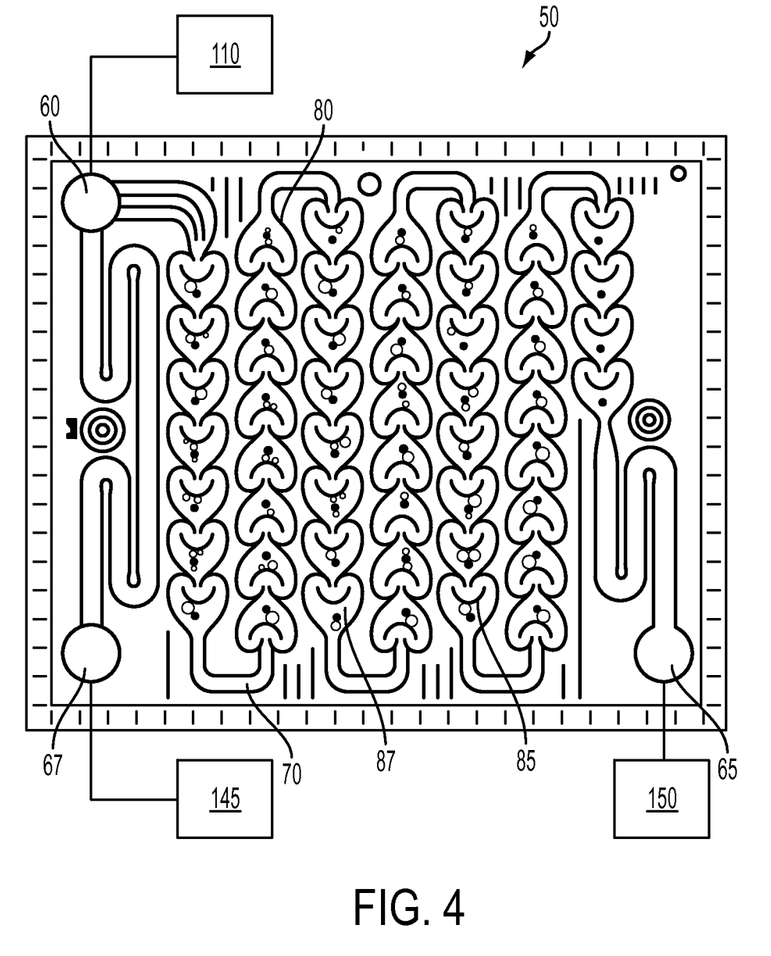
FIG. 4 is a plan view of a reaction volume component of the individual fluidic module of FIG. 1, including schematic representation of fluidic communication of the individual fluidic module with a reactant source, a receiving vessel, and a quenching-fluid source.

Referring now to FIG. 4, an example structural configuration of the reaction volume 50 is shown, as viewed in a plane extending perpendicularly into the plane of FIG. 2 through the middle of the reaction volume 50. The reaction volume 50 comprises the continuous channel 70, which clearly defines a tortuous fluidic flowpath from a reaction-volume inlet 60 of the reaction volume 50 to a reaction-volume outlet 65 of the reaction volume 50. The reaction-volume inlet 60 is schematically shown in FIG. 4 as in fluidic communication with the reactant source 110. Similarly, the reaction-volume outlet 65 is schematically shown as in fluidic communication with the receiving vessel 150. Optionally, as shown in FIG. 4, the reaction volume 50 may comprise a quenching port 67 in fluidic communication with a quenching-fluid source 145.

The continuous channel 70 in the reaction volume 50 may further comprise a plurality of successive mixing chambers 80, shown in FIG. 4 to have a heart-shaped configuration. Each of the successive mixing chambers 80 may comprise one or more flow-diversion structures 85. The flow-diversion structures 85 are configured to split the flow of reactant through each of the successive mixing chambers 80 into two flows that subsequently rejoin in mixing zones 87 behind the flow-diversion structures 85. The two flows thus formed encounter bends in excess of 90° in opposite directions before they are rejoined. Each of the successive mixing chambers 80 has a chamber width greater than the continuous-channel width w (see FIG. 2), the chamber width being measured from the widest portion of the mixing chamber in the direction perpendicular to fluid flow through the continuous channel 70. In preferred embodiments, each of the successive mixing chambers 80 may have a chamber width of from about 10 mm to about 20 mm, measured in the same manner. Without intent to be limited by theory, it is believed that the combination of the flow-diversion structures 85 and the mixing zones 87 in the successive mixing chambers 80 advantageously prevent a phenomenon known as back mixing and, instead allows a phenomenon known as plug flow, similar to the flow produced in a straight tube. These phenomena will be described in greater detail below as particularly advantageous to the sulfonation of DAB. It will be understood that the configuration of the flow-diversion structures 85 is not limited to those depicted in FIG. 4.

It will be understood that the reaction volume 50 is not limited the configuration shown in FIG. 4 and need comprise only a continuous channel defining a tortuous fluidic flow-path. Additional configurations suitable for the reaction volume 50 include those described in European Pat. Appl. EP 2 172 261, entitled "Multiple flow path microfluidic devices," assigned to Corning, Incorporated. Moreover, it will be understood that the reaction volume 50 can be comprise additional fluidic connections (not shown) to configure the reaction volume 50 for use in a continuous-flow microreactor having only one individual fluidic module. In such a configuration, respectively designated portions of the continuous channel 70 may be configured to function as the inlet module, the one or more residence modules, the outlet module, or the quenching module.

Figure 5:
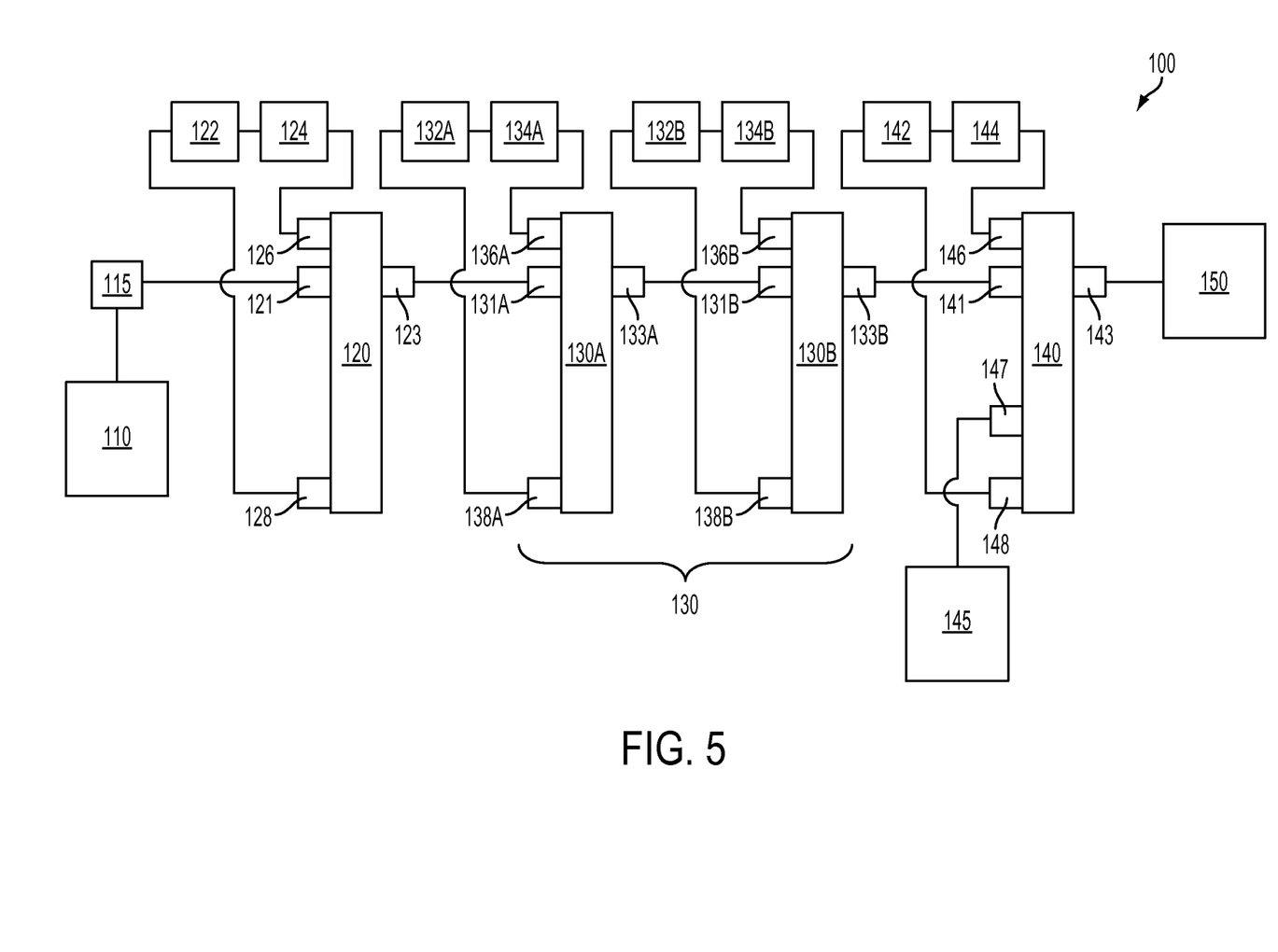
FIG. 5 is a schematic diagram of a continuous-flow microreactor according to an example embodiment of the present invention.

In the context of the continuous-flow process for sulfonating 1,2-diaminobenzene, FIG. 5 shows in schematic form an example embodiment of a continuous-flow microreactor 100 comprising one individual fluidic module or a plurality of sequentially connected individual fluidic modules. One individual fluidic modules is an inlet module 120, at least one individual fluidic module is a residence module 130, and one individual fluidic module is an outlet module 140. Each individual fluidic module is in fluidic communication with a reactant source 110 through an inlet-module inlet 121 of the inlet module 120, and also with a receiving vessel 150 through an outlet-module outlet 143 of the outlet module 140. The inlet-module inlet 121 defines the microreactor inlet, and the outlet-module outlet 143 defines a microreactor outlet. Thus, the microreactor outlet (outlet-module outlet 143) is in fluidic communication with the microreactor inlet (inlet-module inlet 121) through the continuous channels 70 (see FIG. 4) of each of the sequentially connected individual fluidic modules. In preferred embodiments, flow of the sulfonation mixture from the reactant source 110 through the fluidic modules within the continuous-flow microreactor 100 may be precisely controlled by means of a feed pump 115.

The inlet module 120 comprises the inlet-module inlet 121, an inlet-module outlet 123, an inlet-module thermal-control fluid inlet 126, and an inlet-module thermal-control fluid outlet 128. The inlet-module thermal-control fluid inlet 126 and the inlet-module thermal-control fluid outlet 128 are in fluidic communication with an inlet-module control-fluid thermostat 122 and an inlet-module control-fluid pump 124. In isolation the inlet module 120 and its components are configured as detailed above with respect to the individual fluidic module 10 shown and described with reference to FIGS. 1-4.

The inlet module 120 is connected to at least one residence module 130, each residence module also being configured in isolation as detailed above with respect to the individual fluidic module 10 shown and described with reference to FIGS. 1-4. Though FIG. 5 shows a continuous-flow reactor in which the at least one residence module 130 is two residence modules, namely a first residence module 130A and a second residence module 130B, it will be understood that only one residence module may be present or that additional residence modules may be sequentially connected to the two shown. In preferred embodiments, the continuous-flow microreactor 100 may comprise at least three residence modules, and in especially preferred embodiments the continuous-flow microreactor 100 may comprise at least five residence modules.

The first residence module 130A comprises at least a first-residence module inlet 131A, a first-residence module outlet 133A, a first-residence module thermal-control fluid inlet 136A, and a first-residence module thermal-control fluid outlet 138A. Likewise, second residence module 130B comprises at least a second-residence module inlet 131B, a second-residence module outlet 133B, a second-residence module thermal-control fluid inlet 136B, and a second-residence module thermal-control fluid outlet 138B. The first-residence module thermal-control fluid inlet 136A and the first-residence module thermal-control fluid outlet 138A are in fluidic communication with a first-residence module control-fluid thermostat 132A and a first-residence module control-fluid pump 134A. The second-residence module thermal-control fluid inlet 136B and the second-residence module thermal-control fluid outlet 138B are in fluidic communication with a second-residence module control-fluid thermostat 132B and a second-residence module control-fluid pump 134B.

The outlet module 140 comprises at least an outlet-module inlet 141, the outlet-module outlet 143, an outlet-module thermal-control fluid inlet 146, and an outlet-module thermal-control fluid outlet 148. The outlet-module thermal-control fluid inlet 146 and the outlet-module thermal-control fluid outlet 148 are in fluidic communication with an outlet-module control-fluid thermostat 142 and an outlet-module control-fluid pump 144. In isolation, the outlet module 140 and its components are configured as detailed above with respect to the individual fluidic module 10 shown and described with reference to FIGS. 1-4.

In preferred embodiments, at least one individual fluidic module is a quenching module. In FIG. 5, the outlet module 140 is shown to be configured as a quenching module. Even so, it will be understood that, in the alternative, one of the at least one residence module 130 could be a quenching module. Preferably, the quenching module as close as possible to the microreactor outlet (outlet-module outlet 143), such that a maximum number of individual fluidic modules are used to keep the sulfonation reaction active. The quenching module (here, outlet module 140) further comprises a quenching-fluid inlet 147 in fluidic communication with the continuous channel of the quenching module (see FIG. 4). When a quenching module is present, continuous-flow process further comprises introducing a quenching medium from a quenching-fluid source 145 through the quenching-fluid inlet 147, such that the quenching medium mixes with the reactant flow in the continuous channel of the quenching module. The quenching medium may be any fluid (liquid or gas) capable of stopping the sulfonation reaction of DAB in sulfuric acid. In the present continuous-flow process for sulfonating DAB, typically the quenching medium is liquid water.

It will be understood that quenching of the reaction in the sulfonation mixture need not be accomplished by the addition of a quenching medium to the flow of sulfonation mixture in the continuous-flow microreactor 100. Alternatively, quenching of the sulfonation reaction may be accomplished by a thermal quench, whereby the reaction temperature of the outlet module 140, controlled through the operation of the outlet-module control-fluid thermostat 142, may be set to be lower than the reaction temperature in the residence modules 130. In such a configuration for the continuous-flow microreactor 100, the fluidic module chosen to be a quenching module is not configured with a quenching-fluid inlet 147.

It will be apparent that numerous additional configurations are possible for the continuous-flow microreactor 100 and that the embodiment shown in FIG. 5 is but one non-limiting example. For example, though the continuous-flow microreactor 100 in FIG. 5 comprises separate control-fluid thermostats (122, 132A, 132B, and 142) and separate control-fluid pumps (124, 134A, 134B, 144) connected in parallel to each of the respective fluidic modules (120, 130A, 130B, and 140), alternatively the control-fluid inlets and control-fluid outlets of one or more fluidic modules may be connected in series. In a series configuration, the temperature and flow rate of thermal-control fluid through the serially-connected thermal-control volumes of the one or more fluidic modules may be controlled by a single control-fluid thermostat and a single control-fluid pump. In an example embodiment not shown, the inlet module 120 and the residence modules 130 may be thermally regulated by a single control-fluid thermostat (not shown) cooperating with a single control-fluid pump (not shown), while the outlet module 140 is connected to the outlet-module control-fluid thermostat 142 and the outlet-module control-fluid pump 144. In this regard, the parallel-connected thermal-control of the embodiment shown in FIG. 5 represents a maximum amount of precise thermal-control for the sulfonation reaction.

As noted above, in some example embodiments the continuous-flow microreactor 100 may comprise only one individual fluidic module. In this respect, the schematic depiction in FIG. 5 is illustrative of the fluidic connections necessary to configure a microreactor having only one individual fluidic module.

In the continuous-flow process, the sulfonation mixture comprises 1,2-aminobenzene dissolved in a molar excess of sulfuric acid. In the sulfonation reaction, each mole of DAB consumes one mole of sulfuric acid to produce one mole of DBSA. Thus, a molar excess of sulfuric acid requires that the molar ratio of $H_2SO_4$ to DAB in the sulfonation mixture be greater than 1:1. Typically, the molar ratio of $H_2SO_4$ to DAB in the sulfonation mixture is at least 2:1, such as from 2:1 to 10:1. In preferred embodiments, the molar ratio of $H_2SO_4$ to DAB in the sulfonation mixture is at least than 5:1, such as from 5:1 to 10:1.

The sulfonation mixture may be prepared separately from, or as a part of the continuous-flow process by dissolving the 1,2-diaminobenzene in sulfuric acid at an appropriate molar ratio before introducing the sulfonation mixture into the continuous-flow microreactor 100 from the reactant source 110 through the microreactor inlet (inlet-module inlet 121), preferably by means of the feed pump 115. The sulfuric acid is preferably concentrated sulfuric acid, such as 95-97% $H_2SO_4$, based on the weight of the aqueous solution of sulfuric acid being introduced. It is believed that concentrated sulfuric acid may optimize reaction kinetics and prove less costly than use of fuming sulfuric acid or oleum, for example. Sulfuric acid below about 75% $H_2SO_4$ may result in production of DBSA, but yields may be less optimal. Fuming sulfuric acid may be used also but is not preferred. It is believed that an especially high concentration of $SO_3$ in fuming sulfuric acid may complicate the optimization of the continuous-flow microreactor to avoid formation of doubly sulfonated products. Nevertheless, the ability of the present continuous-flow microreactor 100 to produce high-purity DBSA in quantitative yields may be viewed as a distinct advantage over prior-art processes not involving microreactors but requiring the use of expensive and dangerous fuming sulfuric acid or oleum.

The sulfonation mixture may be introduced into the microreactor at a flow rate that may be controlled, for example, by the feed pump 115. Typically, the flow rate may be from about 2 mL/min to about 1500 mL/min, depending on the desired output and the total reactor volume. As used herein, the total reactor volume refers to the total amount of sulfonation mixture that can be retained within the continuous-flow microreactor 100 between the microreactor inlet (inlet-module inlet 121) and the microreactor outlet (outlet-module outlet 143). The continuous-flow microreactor 100 is scalable based on the number of individual fluidic modules and the capacities of each individual fluidic module. Thus, typical reactor volumes may vary significantly, such as from about 10 mL to about 2500 mL, depending on the needs of the user.

The ratio of the total microreactor volume (in mL, for example) to a chosen flow rate (in mL/min, for example) is defined as the residence time (in minutes, for example) of the continuous-flow microreactor 100. Typical residence times may vary from about 10 seconds to about one hour, depending on the configuration of the continuous-flow microreactor 100, particularly with regard to the number of individual fluidic modules and to the reaction volumes of each of the individual fluidic modules. Preferred but non-limiting embodiments of reactor volumes, flow rates, and residence times are provided in TABLE 1. The example data in TABLE 1 are for continuous-flow microreactors comprising a plurality of sequentially connected individual fluidic modules according to the embodiments described above.

TABLE 1

| Volume of each Individual Fluidic Module (mL) | Number of Individual Fluidic Modules in Microreactor | Total Microreactor Volume (mL) | Minimum Flow Rate (mL/min) | Maximum Residence Time (min) | Maximum Flow Rate (mL/min) | Minimum Residence Time (min) |
|---|---|---|---|---|---|---|
| 10 | 3 | 30 | 2.5 | 12 | 250 | 0.12 |
| 10 | 15 | 150 | 2.5 | 60 | 250 | 0.60 |
| 22.5 | 3 | 67.5 | 30 | 2.3 | 450 | 0.15 |
| 22.5 | 15 | 337.5 | 30 | 11.3 | 450 | 0.75 |
| 70 | 3 | 210 | 250 | 0.84 | 750 | 0.28 |
| 70 | 15 | 1050 | 250 | 4.2 | 750 | 1.40 |

TABLE 1-continued

| Volume of each Individual Fluidic Module (mL) | Number of Individual Fluidic Modules in Microreactor | Total Microreactor Volume (mL) | Minimum Flow Rate (mL/min) | Maximum Residence Time (min) | Maximum Flow Rate (mL/min) | Minimum Residence Time (min) |
| --- | --- | --- | --- | --- | --- | --- |
| 150 | 3 | 450 | 500 | 0.9 | 1500 | 0.30 |
| 150 | 15 | 2250 | 500 | 4.5 | 1500 | 1.50 |

The continuous-flow process for sulfonation of DAB further comprises maintaining a reaction temperature of from about 150° C. to about 280° C. in at least the residence modules, preferably in each of the individual fluidic modules, while the sulfonation mixture flows from the microreactor inlet to the microreactor outlet. In preferred embodiments, the reaction temperature is maintained at from about 180° C. to about 220° C. A higher reaction temperature may be advantageous in that the sulfonation reaction will proceed to completion with quantitative yield much more quickly than at lower reaction temperatures. As such, at higher temperatures such as from about 200° C. to about 230° C., residence time may be decreased to as low as about 2 minutes by increasing the chosen flow rate. Though it may be suspected that a higher reaction temperature may make formation of doubly sulfonated impurities more thermodynamic-cally and kinetically favorable, it is believed that the structural advantages inherent in the continuous-flow microreactor 100 nevertheless prevent formation of these impurities, even at high reaction temperatures. Furthermore, it is believed that the maximum reaction temperature may be limited in part by the materials used to form the components of the continuous-flow microreactor including, for example, gaskets and connectors around the individual fluidic modules. Though in preferred embodiments a maximum reaction temperature may be about 220° C., it is contemplated that reaction temperatures as high as 280° C. become readily available for the sulfonation process if the continuous-flow microreactor comprises connectors suitable for use at such a high temperature.

Maintaining the reaction temperature may further comprise circulating a thermal-control fluid through the first thermal-control volume 12 (see FIG. 3) and the second thermal-control volume 14 (see FIG. 3) of each individual fluidic module. Because each individual fluidic module in the continuous-flow microreactor 100 may be equipped with its own thermal-control fluid thermostat (depicted in FIG. 5, 124, 134A, 134B, and 144), the reaction temperature may advantageously be controlled and main-tained independently in each of the individual fluidic modules. This ensures that the sulfonation mixture remains at an optimal reaction temperature during its entire residence in the continuous-flow microreactor 100. The thermal-control fluid may be any readily-available liquid having suitable characteristics to function in a heat exchanging capacity while possessing favorable flow characteristics, such as viscosity, for traversing through the thermal-control volumes of the individual fluidic modules. In example embodiments, the thermal-control fluid is an oil such as silicone oil.

In preferred embodiments, the circulation of the thermal-control fluid is performed while the thermal-control fluid is maintained at a control-fluid temperature equal to the desired reaction temperature such as, for example, from 160° C. to about 230° C., from about 180° C. to about 220° C., or from about 180° C. to about 190° C. Because the progressing reaction of the sulfonation mixture is moderately exothermic, it may be desirable to maintain a control-fluid temperature slightly below the desired reaction temperature so that excess heat from the sulfonation mixture is removed. In further preferred embodiments, the reaction temperature in the quenching module may be set lower than that in the other fluidic modules, independently of the reaction temperatures of the other fluidic modules. This may ensure that the reaction is ended before the sulfonation mixture reaches the receiving vessel 150 and also may prevent any formation of doubly sulfonated impurities. Nevertheless, care must be taken to avoid lowering the reaction temperature in the quenching module low enough to cause DBSA to begin precipitating out of the sulfonation mixture while the sulfonation mixture remains resident in the continuous-flow microreactor 100.

The continuous-flow process for sulfonation of DAB further comprises receiving the sulfonation mixture from the microreactor outlet (outlet-module outlet 143). The sulfonation mixture may be received into any receiving vessel 150 resistant to the corrosive effects of any excess sulfuric acid that may be present when the sulfonation mixture is received.

The continuous-flow process for sulfonation of DAB further comprises precipitating a sulfonated reaction product out of the sulfonation mixture received from the microreactor outlet. The precipitating may comprise, for example, cooling the sulfonation mixture until the sulfonated reaction product forms as a solid precipitate in the sulfonation mixture. In example embodiments, the cooling may comprise exposing the receiving vessel 150 to a cooling bath containing ice water, for example.

The continuous-flow process for sulfonation of DAB, when substantially performed according to the embodiments described above, produces as a sulfonated reaction product DBSA in substantially quantitative yield, free of any doubly sulfonated impurities. Without intent to be limited by theory, it is believed that the continuous-flow microreactor 100, owing in large part to the configuration of the continuous channels of the individual fluidic modules, produces the so-called plug-flow phenomenon, whereby all molecular species in the reactor move forward. Thereby, molecular species that enter the system at substantially the same time are expected to exit the system at substantially the same time, with minimal distribution of residence time, defined above, among the molecular species. As such, the plug-flow phenomenon may prevent any type of back mixing that would be kinetically favorable to the formation of doubly sulfonated impurities in the sulfonated reaction product. Typically, any continuously-stirred tank reactor known in the art is characterized by a very broad distribution of residence time, indicative of substantial back mixing. The extreme example of back mixing is that of a batch-stirred tank reactor, in which all reactants and products remain constantly "back-mixed" in a fixed volume.

Additionally, it is believed that the individual fluidic modules, when configured as described above, in general have superior mixing characteristics that make possible the use of concentrated sulfuric acid in the sulfonation process, as opposed to fuming sulfuric acid. In general, sulfonation of aryl amines occurs by an electrophilic aromatic substitution requiring the formation of $SO_3$ as the active species. The $SO_3$ replaces a hydrogen atom from the aryl ring. Though concentrated sulfuric acid has a non-zero concentration of $SO_3$ in equilibrium with other species, the $SO_3$ concentration is considerably lower than that of fuming sulfuric acid and, therefore, is not typically a preferred choice of reactant in large-scale sulfonation processes.

EXAMPLES

The present invention will be better understood by reference to the following examples, which are offered by way of illustration and which one of skill in the art will recognize are not meant to be limiting.

A sulfonation mixture was prepared by dissolving 160 g (1.48 mol) of 1,2-diaminobenzene in 800 g (435 mL; 8.16 mol) of 95-97% sulfuric acid. In four trials, portions of the sulfonation mixture were pumped through a continuous-flow microreactor comprising sequentially connected individual fluidic modules, specifically an inlet module, five residence modules, and an outlet module, as described above. Each of the individual fluidic modules was held at a constant reaction temperature. The sulfonation mixture was quenched at the reactor outlet with water, and the sulfonated reaction product was precipitated in an ice-water bath. After filtration, the resulting white product was characterized by NMR. In all trials the isolated product was, according to 'H-NMR spectroscopy (400 MHz), free from isomers: (DMSO-$d_6$) δ=6.92 (d, J=8.3 Hz), 7.24 (d/d, J=1.92/8.3 Hz), 7.43 (d, J=1.91 Hz), 8.1 s (broad). Thus, the NMR spectrum was conclusive of the formation of 3,4-diaminobenzenesulfonic acid, free of impurities.

Though in all trials, the only product formed was 3,4-diaminobenzenesulfonic acid, free of impurity, yield of the product was found to vary based on temperature and residence time. A reaction temperature of 160° C. with a residence time of 25 minutes resulted in a yield of 80%. A reaction temperature of 180° C. with a residence time of 5 minutes resulted in a yield of 89%. A reaction temperature of 180° C. with a residence time of 10 minutes resulted in a yield of 90%. A reaction temperature of 180° C. with a residence time of 25 minutes resulted in a yield of 100%.

It is noted that one or more of the following claims use the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A continuous-flow process for sulfonating 1,2-diaminobenzene with 100% yield, the continuous-flow process comprising:
   introducing a sulfonation mixture into a microreactor inlet of a continuous-flow microreactor to produce a flow of the sulfonation mixture through the continuous-flow microreactor, the sulfonation mixture comprising 1,2-aminobenzene dissolved in a molar excess of sulfuric acid, the continuous-flow microreactor comprising one individual fluidic module or a plurality of sequentially connected individual fluidic modules, wherein:
      each individual fluidic module comprises a module inlet and a module outlet, the module inlet being in fluidic communication with the module outlet;
      each individual fluidic module comprises a continuous channel defined in a reaction volume of the individual fluidic module, the continuous channel defining a tortuous fluidic flowpath from a reaction-volume inlet of the reaction volume to a reaction-volume outlet of the reaction volume, the reaction-volume inlet being in fluidic communication with the module outlet, the reaction-volume outlet being in fluidic communication with the module outlet, the continuous channel having a continuous-channel width of from 0.4 mm to 6 mm;
      one individual fluidic module is an inlet module, such that an inlet-module inlet of the inlet module defines the microreactor inlet;
      one individual fluidic module further is an outlet module, such that an outlet-module outlet of the outlet module defines a microreactor outlet;
      at least one individual fluidic module is a residence module providing fluidic communication between the inlet module and the outlet module; and
      the microreactor outlet is in fluidic communication with the microreactor inlet through the continuous channel of each individual fluidic module;
   maintaining a reaction temperature of from 180° C. to about 220° C. in at least the at least one residence module while the sulfonation mixture flows from the microreactor inlet to the microreactor outlet for a total residence time from 25 to 60 minutes;
   receiving the sulfonation mixture from the microreactor outlet; and
   precipitating a sulfonated reaction product out of the sulfonation mixture received from the microreactor outlet.

2. The continuous-flow process of claim 1, wherein at least one of the individual fluidic modules is a quenching module, the quenching module comprising a quenching-medium inlet in fluidic communication with the continuous channel of the quenching module, the method further comprising introducing a quenching medium through the quenching-medium inlet, such that the quenching medium mixes with the reactant flow in the continuous channel of the quenching module.

3. The continuous-flow process of claim 2, wherein the quenching medium is water.

4. The continuous-flow process of claim 1, wherein each individual fluidic module further comprises at least one thermal-control volume in thermal communication with the continuous channel of the same individual fluidic module, the at least one thermal-control volume being in fluidic communication with a thermal-control fluid thermostat, the maintaining of the reaction temperature comprising circulating a thermal-control fluid having a control-fluid temperature of from about 180° C. to about 220° C. through the thermal-control channel of at least the at least one residence module.

5. The continuous-flow process of claim 1, wherein the continuous-flow microreactor comprises at least three sequentially connected individual fluidic modules.

6. The continuous-flow process of claim 5, wherein the continuous-flow microreactor comprises from three to fifteen sequentially connected individual fluidic modules, and a total microreactor volume of the continuous-flow reactor is from 30 mL to 2250 mL.

7. The continuous-flow process of claim 1, wherein the tortuous fluidic flowpath in each individual fluidic module comprises a plurality of bends having bend angles of from 90° to 180°.

8. The continuous-flow process of claim 1, wherein the molar excess of sulfuric acid comprises a molar ratio of $H_2SO_4$ to 1,2-diaminobenzene of from 2:1 to 10:1.

9. The continuous-flow process of claim 1, wherein the molar excess of sulfuric acid comprises a molar ratio of $H_2SO_4$ to 1,2-diaminobenzene of from 5:1 to 10:1.

10. The continuous-flow process of claim 1, wherein the concentrated sulfuric acid is from 95% to 97% $H_2SO_4$ based on the total weight of the sulfuric acid.

11. The continuous-flow process of claim 1, wherein the individual fluidic modules are formed from glass, ceramic, or glass-ceramic.

12. The continuous-flow process of claim 1, wherein the continuous channel in each of the individual fluidic modules has a continuous-channel depth of from 1 mm to 10 mm.

13. The continuous-flow process of claim 1, wherein the continuous channel in each of the individual fluidic modules has a continuous-channel width of from 0.7 mm to 1.1 mm.

14. The continuous-flow process of claim 1, wherein the precipitating comprises cooling the sulfonation mixture until the sulfonated reaction product forms as a solid precipitate in the sulfonation mixture.

15. The continuous-flow process of claim 1, wherein the continuous channel in each individual fluidic module comprises a plurality of successive mixing chambers, each successive mixing chamber comprising at least one flow-diversion structure, each successive mixing chamber having a chamber width greater than the continuous channel width.

16. The continuous-flow process of claim 15, wherein each mixing chamber has a chamber width of from 10 mm to 20 mm.

17. The continuous-flow process of claim 1, wherein the sulfonated reaction product is 3,4-diaminobenzenesulfonic acid free of doubly sulfonated impurities.

18. The continuous-flow process of claim 1, further comprising dissolving the 1,2-diaminobenzene in 95-97% sulfuric acid to form the sulfonation mixture before introducing the sulfonation mixture into the continuous-flow microreactor.

* * * * *